United States Patent
Seow

(10) Patent No.: US 9,986,971 B2
(45) Date of Patent: Jun. 5, 2018

(54) RING LASER FOR USE WITH IMAGING PROBE AS A SAFE MARGIN INDICATOR

(71) Applicant: Covidien LP, Mansfield, MA (US)

(72) Inventor: Chi Min Seow, New Haven, CT (US)

(73) Assignee: Covidien LP, Mansfield, MA (US)

( * ) Notice: Subject to any disclaimer, the term of this patent is extended or adjusted under 35 U.S.C. 154(b) by 1157 days.

(21) Appl. No.: 14/150,345

(22) Filed: Jan. 8, 2014

(65) Prior Publication Data

US 2014/0207002 A1 Jul. 24, 2014

Related U.S. Application Data

(60) Provisional application No. 61/754,158, filed on Jan. 18, 2013.

(51) Int. Cl.
*A61B 8/00* (2006.01)
*A61B 8/12* (2006.01)

(52) U.S. Cl.
CPC .............. *A61B 8/4416* (2013.01); *A61B 8/12* (2013.01); *A61B 8/445* (2013.01); *A61B 8/4444* (2013.01)

(58) Field of Classification Search
CPC combination set(s) only.
See application file for complete search history.

(56) References Cited

U.S. PATENT DOCUMENTS

| | | |
|---|---|---|
| 5,628,327 A | 5/1997 | Unger et al. |
| 5,792,215 A | 8/1998 | Martin et al. |
| 5,810,841 A | 9/1998 | McNeirney et al. |
| 5,976,092 A | 11/1999 | Chinn |
| 6,095,981 A | 8/2000 | McGahan |
| 6,096,049 A | 8/2000 | McNeirney et al. |
| 6,176,835 B1 | 1/2001 | Pachal |
| 6,443,960 B1 | 9/2002 | Brabrand et al. |
| 6,954,667 B2 | 10/2005 | Treado et al. |
| 6,965,793 B2 | 11/2005 | Treado et al. |
| 7,945,312 B2 | 5/2011 | Hular et al. |
| 7,999,928 B2 | 8/2011 | Beckstead et al. |
| 8,162,852 B2 | 4/2012 | Norris |
| 2004/0220478 A1 | 11/2004 | Wallace et al. |
| 2008/0269778 A1 | 10/2008 | Patti |
| 2009/0118742 A1 * | 5/2009 | Hartmann .......... A61B 17/1703 606/130 |
| 2009/0299218 A1 | 12/2009 | Holler et al. |
| 2009/0318756 A1 * | 12/2009 | Fisher ...................... A61B 1/04 600/109 |
| 2010/0106015 A1 | 4/2010 | Norris |
| 2010/0125172 A1 * | 5/2010 | Jayaraj ..................... A61B 1/06 600/249 |
| 2011/0015542 A1 | 1/2011 | Hibner et al. |
| 2012/0010568 A1 * | 1/2012 | Smith ............... A61M 5/31591 604/134 |
| 2012/0022357 A1 | 1/2012 | Chang et al. |
| 2012/0088991 A1 | 4/2012 | Nachabe et al. |
| 2014/0088371 A1 * | 3/2014 | Vayser ............... A61B 1/00135 600/249 |

* cited by examiner

*Primary Examiner* — Christopher Cook

(57) ABSTRACT

A surgical imaging apparatus is disclosed, and includes an elongate body having a proximal portion and a distal portion and including at least one ultrasonic transducer. The surgical imaging apparatus also includes at least one light source being operatively coupled with the elongate body and configured to move relative to the elongate body. The at least one light source is configured to project light onto a tissue surface. The light is dimensioned to illuminate a section of tissue corresponding to a tissue margin.

20 Claims, 5 Drawing Sheets

RING LASER FOR USE WITH IMAGING PROBE AS A SAFE MARGIN INDICATOR

CROSS-REFERENCE TO RELATED APPLICATIONS

This application claims the benefit of and priority to U.S. Provisional Patent Application No. 61/754,158, filed Jan. 18, 2013, the entire disclosure of which is incorporated by reference herein.

BACKGROUND

1. Technical Field

The present disclosure relates to a surgical imaging apparatus for imaging tissue structures with ultrasonic energy, and in particular to a surgical imaging apparatus configured for illuminating a section of imaged tissue which may be on the surface or the in the subsurface of a tissue structure.

2. Discussion of Related Art

Today, many surgical procedures are performed through small openings in the skin, as compared to the larger openings typically required in traditional procedures, in an effort to reduce both trauma to the patient and recovery time. Generally, such procedures are referred to as endoscopic, unless performed on the patient's abdomen, in which case the procedure is referred to as laparoscopic. Throughout the present disclosure, the term minimally invasive should be understood to encompass both endoscopic and laparoscopic procedures.

During the course of minimally invasive procedures, the nature of the relatively small opening through which surgical instruments are manipulated, and/or the presence of sub-surface structures, may obscure a direct line-of-sight to the target surgical site. Even dedicated visualization tools, e.g., cameras, endoscopes, and the like, may be limited by the geometry of a minimally invasive surgical site. Accordingly, it would be desirable to provide a method of sub-surface visualization that is not limited by the geometry of the minimally invasive surgical site.

One such technique is the use of ultrasound imaging to provide clinicians with the ability to image sub-surface structures. Ultrasound imaging relies on different acoustic impedances of adjacent tissue structures to provide the contrast used for imaging and identifying separate tissue structures. Ultrasound imaging possesses several advantages that are attractive for real-time application in surgical procedures, e.g., minimal associated radiation and relatively small and inexpensive imaging hardware. Further, imaging data obtained from ultrasound imaging procedures is collected instantly and at localized points within a patient, as opposed to collected from a large imaging vessel in which a patient is positioned.

In ultrasound imaging procedures, it may be desirable to define an area or region of tissue, e.g., a diseased portion of the tissue or a safe margin surrounding the diseased portion of tissue, or for further analysis or to focus on a desired site for ongoing minimally invasive procedures. Accordingly, it would be desirable to provide an ultrasound imaging apparatus that is configured to illuminate an area or define region of tissue with visible light, e.g., a safe tissue margin surrounding a diseased, e.g., cancerous region of tissue.

SUMMARY

The present disclosure, in accordance with various embodiments thereof, is directed to a surgical imaging apparatus.

According to one aspect of the present disclosure surgical imaging apparatus is disclosed, and includes an elongate body having a proximal portion and a distal portion and including at least one ultrasonic transducer. The surgical imaging apparatus also includes at least one light source being operatively coupled with the elongate body and configured to move relative to the elongate body. The at least one light source is configured to project visible light onto a tissue surface. The light is dimensioned to illuminate a section of tissue corresponding to a tissue margin. The at least one light source may be configured to project a laser beam.

According to another aspect of the present disclosure, a leadscrew is operably coupled with the at least one light source. The at least one light source may be configured to threadably engage the leadscrew. The at least one light source may be configured to move along the elongate body in response to movement of the leadscrew.

According to another aspect of the present disclosure, the leadscrew is operatively coupled with a motor. In one aspect of the present disclosure, the light projected onto the tissue surface has a circular profile. In still another aspect of the present disclosure, the at least one light source is configured to project light such that a tissue defect is disposed substantially at the center of the projected light. In yet another aspect of the present disclosure, the at least one light source is configured such that movement of the at least one light source relative to the elongate body changes the dimension of the light projected onto the tissue surface.

According to another aspect of the present disclosure, a surgical imaging apparatus is disclosed, and includes an imaging probe having an elongate body. The elongate body includes an ultrasound transducer, a leadscrew, and a light source threadably coupled with the leadscrew. The light source is configured to project light onto a tissue surface at a first dimension. The light source is configured for movement along the imaging probe such that the light source projects light onto the tissue surface at a second dimension being different from the first dimension. The light source is configured to be moved along the imaging probe to project light onto tissue at the second dimension in response to information received from the ultrasound transducer. The light source may project a laser beam.

According to another aspect of the present disclosure, the elongate body of the imaging probe defines an interior channel in which the leadscrew is disposed. According to another aspect of the present disclosure, the light source includes an emitter at least partially exposed outside the elongate body. According to still another aspect of the present disclosure, the elongate body defines a slot through which a portion of the light source is configured to translate. According to yet another aspect of the present disclosure, the imaging probe is configured to be coupled with a processor. In another aspect of the present disclosure, the light source is configured to project light in a circular configuration.

According to another aspect of the present disclosure, a method of illuminating a tissue surface is disclosed, and includes providing a surgical imaging apparatus. The surgical imaging apparatus includes an elongate body, a leadscrew, and a light source. The elongate body defines a channel therein, and the leadscrew is disposed within the channel. The light source is configured to project light onto a first area of a tissue surface. The light source is threadably coupled with the leadscrew. The method includes rotating the leadscrew such that the light source translates along the leadscrew to project light onto a second area of the tissue surface, the second area being different than the first area. In another aspect of the present disclosure, the method includes providing an ultrasonic transducer configured to receive ultrasonic energy. In still another aspect of the present disclosure, the leadscrew is rotated such that the light source illuminates the second area of tissue in response to a signal received from the ultrasonic transducer.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure.

DETAILED DESCRIPTION OF THE DRAWINGS

Figure 1:
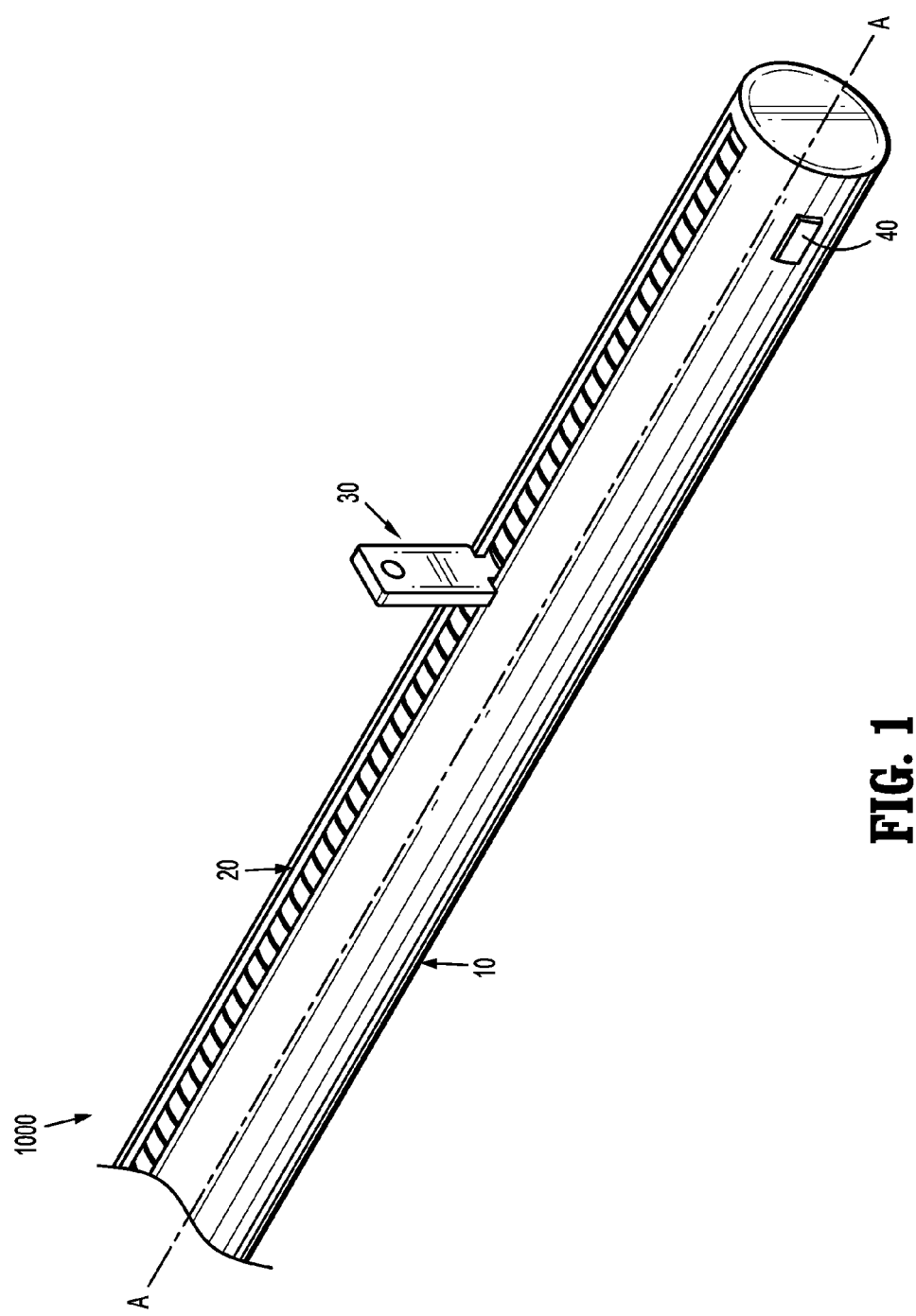
FIG. 1 is a perspective view of a surgical imaging apparatus according to the present disclosure.

Embodiments of the presently disclosed surgical imaging apparatus will now be described in detail with reference to the figures, in which like reference numerals identify corresponding elements throughout the several views.

Referring initially to FIG. 1, a surgical imaging apparatus is generally designated as 1000. Surgical imaging apparatus 1000 may be, e.g., an imaging probe, and includes an elongate body 10 having a proximal portion and a distal portion, and defining a longitudinal axis "A". The elongate body 10 of the surgical imaging apparatus 1000 may have a substantially straight profile, as shown, and is configured for disposition in a minimally invasive surgical site, as will be discussed further below. Surgical imaging apparatus 1000 also includes at least one light source 30. Light source 30 is operably coupled with a leadscrew 20, and is configured to translate substantially along the leadscrew 20 such that the light source 30 moves along the elongate body 10, as will be described further below. In this manner, light source 30 is operably coupled with the elongate body 10. Surgical imaging apparatus 1000 also includes an ultrasound transducer 40.

Figure 2:
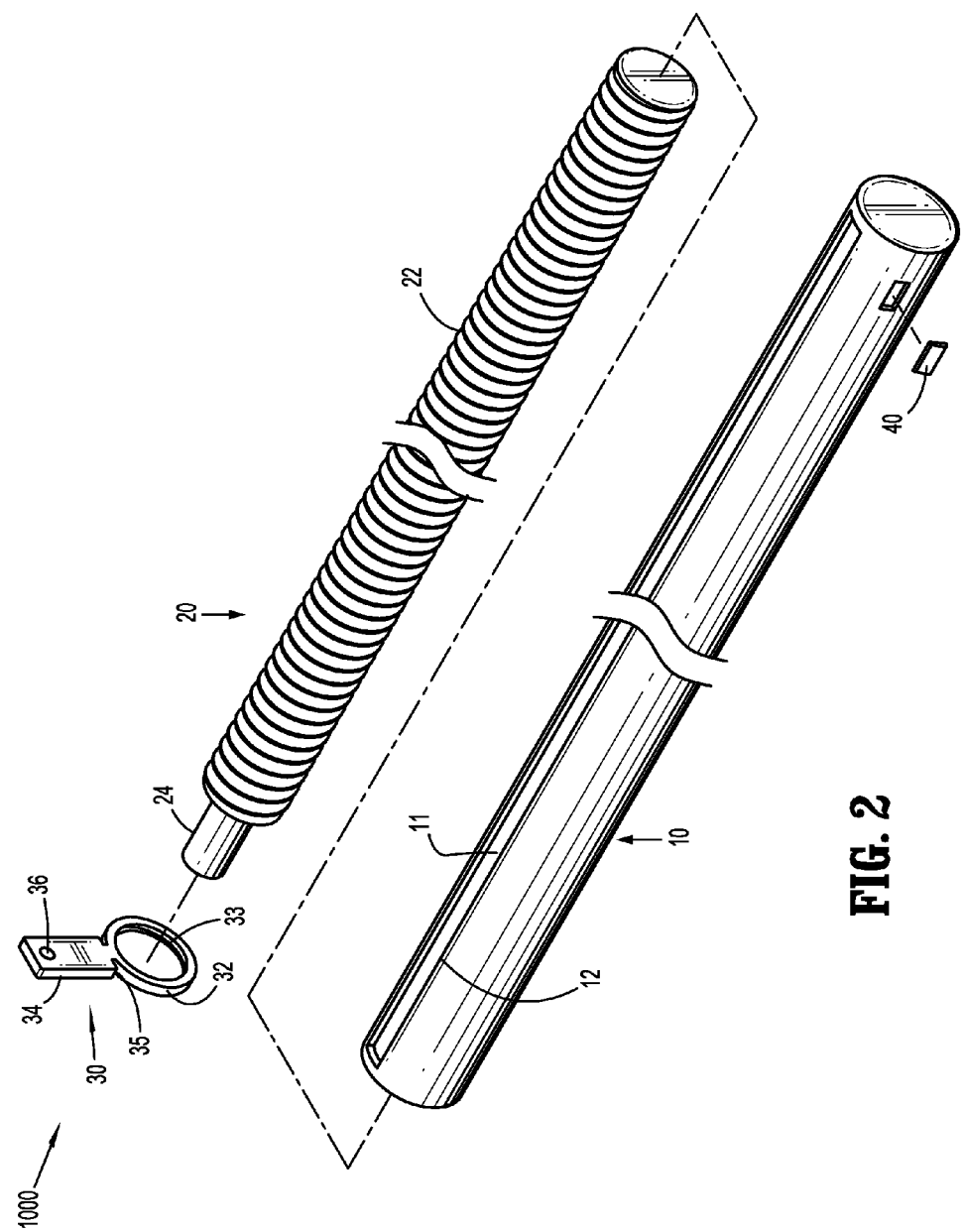
FIG. 2 is a parts-separated view of the surgical imaging apparatus.

Turning now to FIG. 2, the components of the surgical imaging apparatus 1000 are shown in parts-separated view. Elongate body 10, as shown, may have a substantially straight, tubular profile that defines a channel 11 therein, and includes a slot 12 extending substantially the length of the elongate body 10 along an outer wall thereof. Slot 12 may extend through the proximal end of the elongate body 10, and terminate a distance spaced away from the distal end of the elongate body 10.

Leadscrew 20, as shown, has a substantially elongate, tubular profile, and is configured for disposition within the channel 11 of the elongate body 10. Accordingly, leadscrew 20 may define a cross-sectional dimension that is smaller than a cross-sectional dimension of the elongate body 10. Leadscrew 20 defines an outer thread 22 extending substantially along the entire length thereof. A proximal portion of the leadscrew 20 may include a driving portion 24 for coupling with a tool or driver, as will be described further below. Outer thread 22 may be helically wound, and may have any desirable configuration, e.g., a single or double threaded configuration.

Light source 30, as shown includes an engagement portion 32, a projection portion 34, and a neck 35 defined therebetween. Engagement portion 32 may be a substantially annular member, as shown, and defines an internal threading 33 that is configured to interengage the outer thread 22 of the leadscrew 20, as will be described further below. Neck 35 is a narrowed portion of light source 30 that is dimensioned to translate through the slot 12 of the elongate body 10, as will be described further below. Projection portion 34 is an elongate, tab-like member that extends laterally away from the neck 35, and includes an emitter 36. Emitter 36 is configured to be at least partially exposed outside the elongate body 10, as will be described further below.

Emitter 36 is an optical element that is configured to transmit light therefrom. Accordingly, emitter 36 may be a substantially transparent element, e.g., a polymer or glass, that is configured to project light therethrough. Accordingly, emitter 36 may include a light-projecting element, e.g., an L.E.D. or laser diode. Emitter 36 is positioned on projection portion 24 such that emitter 36 transmits light substantially along and laterally spaced from the longitudinal axis A. Emitter 36 may be configured to transmit light in a predetermined pattern.

Ultrasound transducer 40 may be any type of transducer or sensor that is configured to detect the presence and/or magnitude of ultrasonic energy. Accordingly, ultrasound transducer 40 is configured to convert ultrasonic energy reflected off tissue structures having different acoustic impedances into electrical signals, as will be described further below. In embodiments, ultrasound transducer 40 may be configured to generate or transmit ultrasonic energy. Ultrasound transducer 40 may be removably or fixedly mounted on an outer surface of the elongate body 40. Elongate body 10 may include a recess for receiving the ultrasound transducer 40. In some embodiments, ultrasound transducer 40 may be mounted on a different portion of the elongate body 10, e.g., an interior portion of elongate body 10. In still other embodiments, ultrasound transducer 40 may be separate from elongate body 10.

It will be understood that the components of surgical imaging apparatus 1000 may have any desirable configuration or arrangement, and may be formed of any suitable materials for their respective purposes, e.g., biocompatible polymers, metals, or composites. It will further be understood that while surgical imaging apparatus 1000 has been described with respect to use in minimally invasive procedures, the presently disclosed surgical imaging apparatus is suitable for use in traditional open-type surgical procedures.

Figure 3:
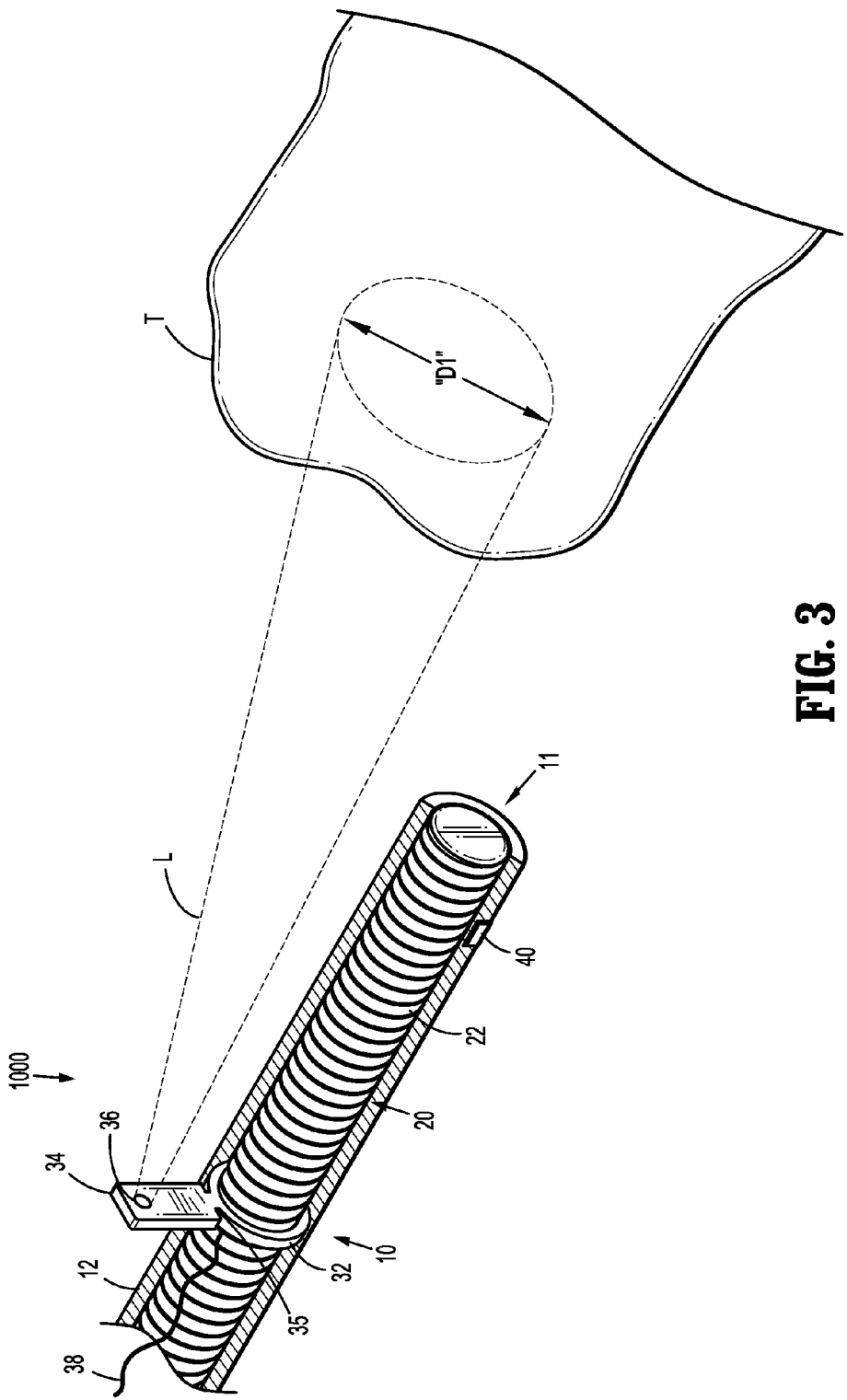
FIG. 3 is a cutaway view of the surgical imaging apparatus projecting light toward a tissue surface.

Turning now to FIG. 3, surgical imaging apparatus 1000 is shown in assembly. In this manner, surgical imaging apparatus 1000 defines a probe-like member for use in minimally invasive procedures. Leadscrew 20 is shown disposed within the channel 11 defined within the elongate body 10. The engagement portion 32 of the light source 30 is threadably engaged with the leadscrew 20. A clearance is defined between the leadscrew 20 and the inner surface of the elongate body 10 such that the engagement portion 32 of the light source 30 is disposed within the channel 11 of the elongate body 10. The engagement portion 32 of the light source 30 is substantially free from interference with the inner surface of elongate body 10 such that the engagement portion 32 is free to move longitudinally within the channel 11, as will be described further below.

Slot 12, is dimensioned to abut the lateral sides of the neck 35 defined between the engagement portion 32 and the projection portion 34 of the light source 30. In this manner, the neck 35 of the light source 30 is disposed between the walls of the slot 12 of the elongate body 10, while the projection portion 34 of the light source 30, extending therefrom, is disposed laterally away and in transverse relation to the elongate body 10. The neck 35 may be substantially free from frictional engagement with the walls of the slot 10, or may engage the walls of the slot 12, e.g., to prevent slippage or to provide a predetermined resistance to movement.

As described above, the emitter 36 of the light source 30 is configured to project light "L" onto a tissue surface "T". Light L may be any type of light configured to illuminate portions of the tissue surface T. As shown, light L may be a laser beam. Emitter 36 may be configured to project light L in a predetermined pattern along the tissue surface T. As shown, emitter 36 may project light L in a circular or ring-like pattern. Light L disperses, i.e., widens, as it is transmitted away from the emitter 36. Accordingly, light L strikes the tissue surface T over an area larger than the surface area defined by emitter 36. In this manner, light L illuminates an area of the tissue surface T such that the light L defines a diameter "D1" corresponding to a section of the tissue surface T. As described above, the area of tissue surface T that is illuminated by light L may correspond to an area of tissue T containing a tissue defect, e.g., a diseased or cancerous portion of tissue, and a safe tissue margin surrounding it, i.e., a margin defined outside the diseased portion of tissue such that removal of the diseased portion of tissue and the surrounding safe margin of tissue will minimize the spread of disease or cancer to remaining tissue. In this manner, light L is configured to illuminate the outer perimeter of a safe margin of tissue, wherein a tissue defect is disposed substantially at the center of the safe margin of tissue.

Emitter 36, as shown, may draw electrical power to project light L from an electrical wire 38 electrically coupled with the light source 30. Electrical wire 38 may be any type of cable or conduit suitable for transmitting electrical energy between the emitter 36 and a source of electrical energy, e.g., a battery, generator, or local power grid (not shown). In embodiments, a portable source of electrical energy, e.g., a capacitor or inductor, may be incorporated into surgical imaging apparatus 1000 and electrically coupled with the laser light source 30.

Figure 4:
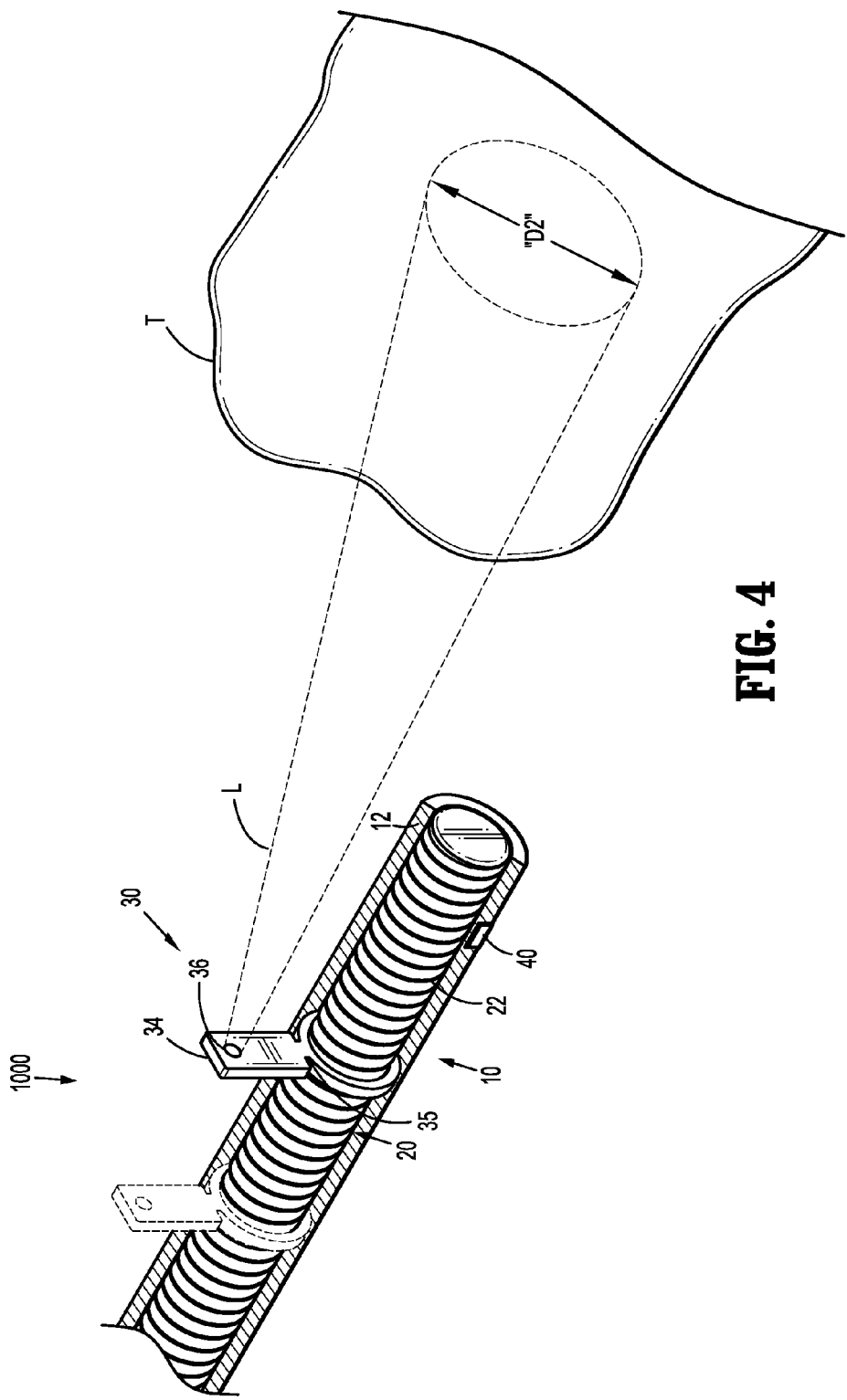
FIG. 4 is a cutaway view of the surgical imaging apparatus, with a light source being moved in relation to a tissue surface.

Turning now to FIG. 4, the surgical imaging apparatus 1000 is shown with the light source 30 being moved longitudinally along the elongate body 10. As described above, the light source 30 is threadably engaged with the leadscrew 20. Because the slot 12 of the elongate body 10 is dimensioned such that the neck 35 of the light source 30 substantially abuts the lateral sides of the slot 12, as the leadscrew 20 rotates within the elongate body 10, the light source 30 is maintained in a substantially constant radial orientation relative to the longitudinal axis A. In this manner, as the leadscrew 20 rotates within the elongate body 10, the outer thread 22 of the leadscrew 20 interengages the thread 33 defined in the engagement portion 32 of the light source 30 such that the engagement portion 32 moves proximally or distally along the leadscrew 20. The leadscrew 20 is configured to rotate within the elongate body 10, but remains axially stationary with respect to the elongate body 10. Accordingly, the neck 35 of the light source 30 moves proximally or distally through the slot 12 of the elongate body 10, and the projection portion 34 of the light source 30, extending laterally therefrom, moves proximally or distally along the elongate body 10. Thus, as the leadscrew 20 rotates within the elongate body 10, the projection portion 34 of the light source 30, and the emitter 36 carried thereon, move along the elongate body 10, as shown. In embodiments, the surgical imaging apparatus 1000 may include a washer or other low-friction element to minimize friction between the rotating leadscrew 20 and the inner surface of the elongate body 10. In other embodiments, a lubricant may be provided to minimize friction between the rotating leadscrew 20 and the inner surfaces of the elongate body 10.

The light L projected by the emitter 36 is configured such that as the emitter 36 moves along the elongate body 10, the area of tissue T that is illuminated by the light L changes due to the changed distance over which the light L disperses before reaching tissue surface T. As shown, distal movement of the emitter 36 causes the light L to a region of the tissue surface T having a dimension "D2". In this manner, the rotation of the leadscrew 20 causes the dimension of the light L to change such that a different-sized region of tissue T is illuminated by the light source 30.

As described above, the region of tissue T that is illuminated by the light source 20 may correspond to a safe margin for removal of tissue. In this manner, the light L provides a visual indication of the outer perimeter of a safe margin of tissue, e.g., for ongoing imaging or analysis, or for aiding an operator in tissue dissection or removal. Accordingly, light source 30 is configured for movement along the elongate body 10 such that the region of the tissue T illuminated by light L may be adjusted according to the needs of the minimally invasive procedure to be performed.

Figure 5:
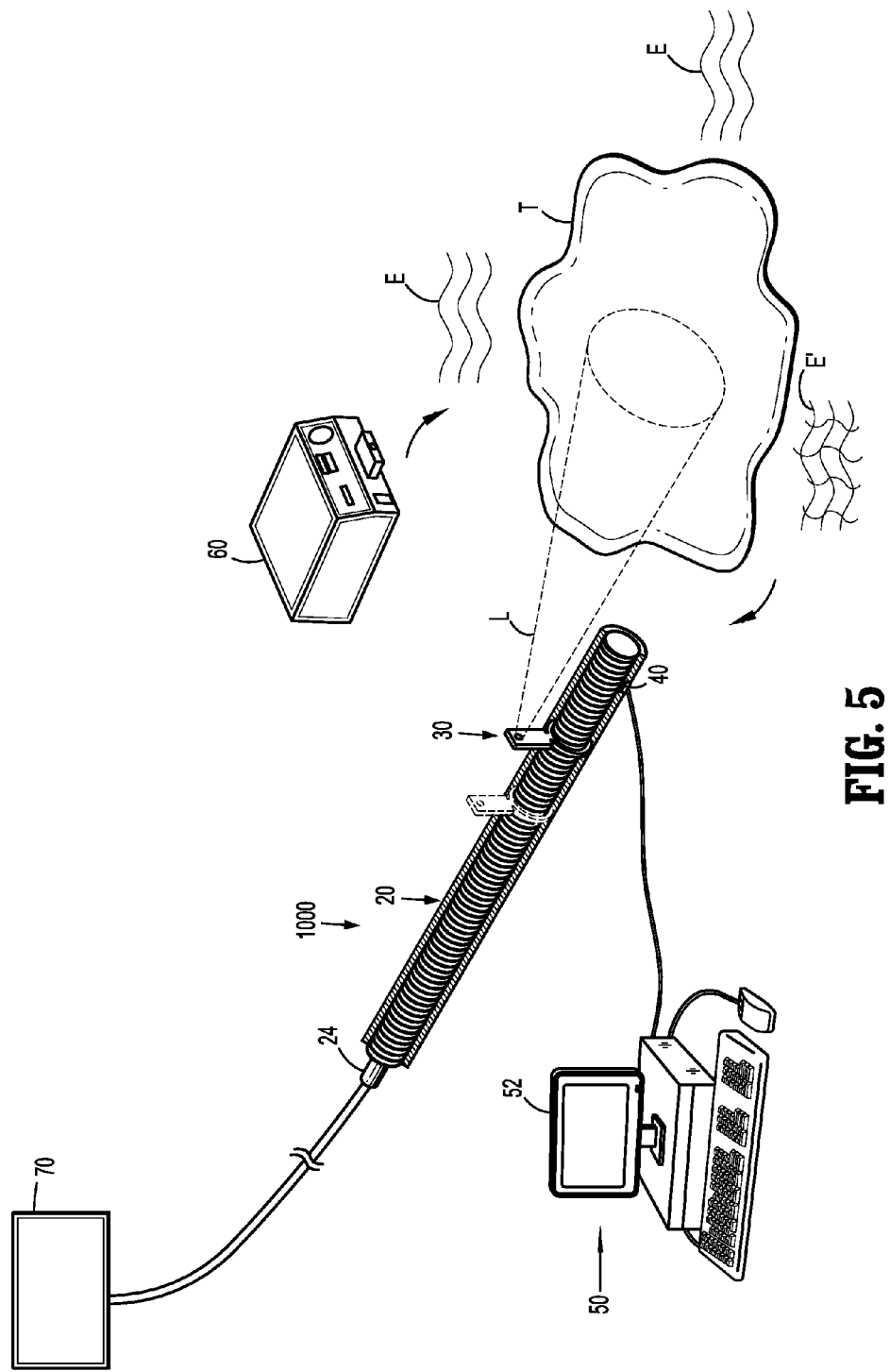
FIG. 5 is a cutaway view of the surgical imaging apparatus being connected with an ultrasonic transducer, a processor, and a motor.

Referring to FIG. 5, the surgical imaging apparatus 1000 is shown coupled with a processor 50. An ultrasound generator 60 is provided, and is configured to generate and transmit ultrasonic energy "E", e.g., an ultrasonic wave, to a minimally invasive surgical site. Accordingly, ultrasound generator 60 is configured to produce and/or transmit ultrasonic energy E having a frequency of at least about 20 kHz. In some embodiments, ultrasound transducer 40 may be configured to generate and transmit ultrasonic energy E to a surgical site.

As ultrasonic energy E is transmitted into a minimally invasive surgical site, ultrasonic energy E interacts with tissue structures, and is reflected therefrom. Accordingly, reflected ultrasonic energy E' is reflected off tissue structures, e.g., tissue surface T.

Ultrasound transducer 40, as described above, is configured to receive ultrasound energy E and produce an electrical signal based on the reflected ultrasonic energy E' received. Accordingly, as the reflected ultrasonic energy E' received from different tissue structures has different properties based on the acoustic impedance of different tissue structures, ultrasonic transducer 40 has produced different electrical signals in response to the reflected ultrasonic energy E' received from those structures.

Ultrasonic transducer 40 is also coupled to processor 50, which is configured to interpret the electrical signals received from ultrasonic transducer 40. Accordingly, processor 50 may include a monitor 52 for displaying stored or real-time data, e.g., 2D- or 3D- visual or graphical representations of data collected by the ultrasound transducer 40. In this manner, processor 50 provides an interface, externally of a patient, that enables an operator to visualize the various structures within a body cavity.

Processor 50 may be configured to produce signals in response to the data provided by the ultrasound transducer 40. If the processor 50 detects a shift in the positioning of the tissue surface T in relation to the surgical imaging apparatus 1000, the processor 50 may provide an indication that the light source 30 should be moved along the elongate body 10 to maintain the illumination of the section tissue surface T corresponding to a safe tissue margin. In some embodiments, the processor 50 may detect a changed condition at the minimally invasive surgical site, e.g., a growth or spreading of a diseased portion of tissue, such that the dimension of a safe tissue margin has changed. Such indications may be provided on the monitor 52. Additionally, processor 50 may incorporate a memory storage module, e.g., an onboard or removable memory storage device, EEPROM, or the like, for storing data received from the ultrasonic transducer 40, or for comparison with predetermined values or for providing feedback.

As described above, the leadscrew 20 may include a driving portion 24 configured for coupling with, e.g., a manual or powered driving tool. Accordingly, driving portion 24 may include surface features for intercooperating with a driving tool, e.g., a hexagonal head or slot for receiving a driving tool (not shown). Driving portion 24 may be operably coupled with a motor 70 as shown. Motor 70 is electrically coupled with the processor 50 such that a signal produced by the processor 50 in response to a changed condition at the minimally invasive surgical site causes the motor 70 to rotate the leadscrew 20 and cause the light source 30 to move along the elongate body such that the light L illuminates a portion of the tissue surface T to define a safe tissue margin.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims.

The invention claimed is:

1. A surgical imaging apparatus, comprising:
   an elongate body having a proximal portion and a distal portion and including an ultrasonic transducer;
   a light source operatively coupled with the elongate body and configured to move relative to the elongate body, wherein the at least one light source is configured to project light onto a tissue surface, the light projected onto a tissue surface is dimensioned to illuminate a section of tissue corresponding to a tissue margin; and
   a processor in communication with the ultrasonic transducer and the light source, the processor configured to receive a signal from the ultrasonic transducer indicative of a change in size of the tissue margin and move the light source according to the signal received from the ultrasonic transducer to illuminate a section of tissue corresponding to the change in size of the tissue margin.

2. The surgical instrument of claim 1, wherein the light source is configured to project a laser beam.

3. The surgical instrument of claim 1, further comprising a leadscrew operably coupled with the light source.

4. The surgical instrument of claim 3, wherein the light source is configured to threadably engage the leadscrew.

5. The surgical instrument of claim 4, wherein the light source is configured to move along the elongate body in response to movement of the leadscrew.

6. The surgical instrument of claim 5, wherein the leadscrew is operably coupled with a motor.

7. The surgical instrument of claim 1, wherein the light projected onto the tissue surface has a circular profile.

8. The surgical instrument of claim 1, wherein the light source is configured to project light such that a tissue defect is disposed substantially at the center of the projected light.

9. The surgical instrument of claim 1, wherein the light source is configured such that movement of the light source relative to the elongate body changes the dimension of the light projected onto the tissue surface.

10. The surgical instrument of claim 1, wherein the ultrasonic transducer is configured to detect an increase or decrease in size of a diseased portion of tissue during a surgical procedure and the processor is configured to move the light source to increase or decrease a size of an area that is illuminated corresponding to the detected increase or decrease in size of the diseased portion of tissue.

11. A surgical imaging apparatus, comprising:
    an imaging probe having an elongate body and including:
       an ultrasound transducer;
       a leadscrew; and
       a light source threadably coupled with the leadscrew, the light source configured to project light onto a tissue surface at a first dimension, wherein the light source is configured for movement along the imaging probe such that the light source projects light onto the tissue surface at a second dimension, the second dimension being different from the first dimension; and
    a processor in communication with the ultrasound transducer and the leadscrew, wherein the processor is configured to receive a signal from the ultrasound transducer indicative of a change in size of a tissue margin and rotate the leadscrew, and therefore move the light source to project light onto the tissue at the second dimension according to the signal received from the ultrasound transducer to illuminate a section of tissue corresponding to the change in size of the tissue margin.

12. The surgical imaging apparatus of claim 11, wherein the light source projects a laser beam.

13. The surgical imaging apparatus of claim 11, wherein the elongate body of the imaging probe defines an interior channel in which the leadscrew is disposed.

14. The surgical imaging apparatus of claim 13, wherein the light source includes an emitter at least partially exposed outside the elongate body.

15. The surgical imaging apparatus of claim 14, wherein the elongate body defines a slot through which a portion of the light source is configured to translate.

16. The surgical imaging apparatus of claim 11, wherein the light source is configured to project light in a circular configuration.

17. The surgical imaging apparatus of claim 11, wherein the ultrasound transducer is configured to detect an increase or decrease in size of a diseased portion of tissue during a surgical procedure and the processor is configured to move the light source to increase or decrease a size of an area that is illuminated corresponding to the detected increase or decrease in size of the diseased portion of tissue.

18. A method of illuminating a tissue surface, comprising:
    projecting light from a light source onto a tissue surface corresponding to a first tissue margin, the light source threadably coupled to a leadscrew disposed within a channel defined within an elongate body of a surgical imaging apparatus;
    receiving a signal from an ultrasound transducer corresponding to a change in size of the tissue margin using a processor in communication with the ultrasound transducer and the leadscrew;

rotating the leadscrew according to the signal received from the ultrasound transducer such that the light source translates along the leadscrew to project light onto the tissue surface corresponding to a second tissue margin, the second tissue margin being different than the first tissue margin.

19. The method according to claim 18, further including detecting an increase or decrease in size of a diseased portion of tissue using the ultrasound transducer.

20. The method according to claim 19, wherein receiving a signal from the ultrasound transducer includes receiving a signal corresponding to an increase or decrease in the size of the tissue margin based on the detected increase or decrease in size of the diseased portion of tissue.

* * * * *